(12) United States Patent
Corti

(10) Patent No.: US 7,025,592 B2
(45) Date of Patent: Apr. 11, 2006

(54) BONE-DISLOCATING DEVICE

(76) Inventor: Guido Corti, Via Bellaria 34, I - 40139 Bologna (IT)

(*) Notice: Subject to any disclaimer, the term of this patent is extended or adjusted under 35 U.S.C. 154(b) by 92 days.

(21) Appl. No.: 10/402,715

(22) Filed: Mar. 28, 2003

(65) Prior Publication Data
US 2003/0186194 A1    Oct. 2, 2003

(30) Foreign Application Priority Data
Mar. 29, 2002 (IT) .................... MI20020173 U

(51) Int. Cl.
A61C 3/00 (2006.01)

(52) U.S. Cl. .................................... 433/153
(58) Field of Classification Search ............ 433/153, 433/158, 161, 148, 149; 606/105, 90; 254/104; 144/195.5, 195.8; 269/219
See application file for complete search history.

(56) References Cited

U.S. PATENT DOCUMENTS

| 153,009 | A | * | 7/1874 | Nesbitt | 254/104 |
| 296,622 | A | * | 4/1884 | Reno | 269/219 |
| 819,136 | A | * | 5/1906 | Herman | 433/149 |
| 1,137,109 | A | * | 4/1915 | Arneson | 269/219 |
| 1,197,648 | A | * | 9/1916 | Meyers | 433/158 |
| 1,370,994 | A | * | 3/1921 | Pomerenke | 269/219 |
| 6,309,220 | B1 | | 10/2001 | Gittleman | |

FOREIGN PATENT DOCUMENTS

| CH | 656295 A5 * | 6/1986 |
| DE | 197 32 983 A1 | 2/1999 |
| DE | 199 49 385 A1 | 4/2001 |
| FR | 2 532 171 | 3/1984 |

OTHER PUBLICATIONS

Article 1 Continuing Education XP-002118818 "The Osteotome Technique: Part 2 —The Ridge Expansion Osteotomy (REO) Procedure" Robert B. Summers, pp. 422-434.

* cited by examiner

Primary Examiner—Todd E. Manahan
(74) Attorney, Agent, or Firm—Hedman & Costigan

(57) ABSTRACT

A bone-dislocating device suitable for being inserted in a bone to be dislocated (16), in particular a maxillary or jaw bone, comprises a wedged body (12), subdivided into two parts (12a and 12b) substantially having a triangular section, said wedged body (12) being equipped with driving elements (17) close to an upper end, for spacing the two parts (12a and 12b) of the wedged body (12).

1 Claim, 1 Drawing Sheet

BONE-DISLOCATING DEVICE

The present invention relates to a bone-dislocating device, in particular a bone dislocator used in dental surgery.

In dental surgery, it may be necessary to intervene on the maxillary or jaw bone separating it to a certain extent in the intervention point for the correction of bone defects, even minimum.

Bone defects can be particularly found in patients remaining for a long period without one or more dental elements, thus being exposed to bone re-absorption phenomena even of a considerable degree. When the residual bone has an insufficient thickness, it is not possible to insert oral osteo-integrated plants, which substitute the missing dental element.

Bone dislocation is currently effected by means of osteotomy or splint-crest techniques using so-called bone scalpels.

The main disadvantage concerns the high degree of trauma following the intervention and the risk of causing fractures in the bone to be dislocated or even necrosis.

An objective of the present invention is to provide a bone-dislocating device which acts with the least possible trauma and invasiveness.

Another objective of the present invention is to provide a bone-dislocating device which can be activated progressively and at entities which can be programmed.

A further objective of the present invention is to provide a particularly simple and functional dislocating device, with reduced costs.

These objectives according to the present invention are achieved with a bone-dislocating device as illustrated in claim 1.

Further characteristics of a dislocating device are object of the dependent claims.

The characteristics and advantages of a bone-dislocating device according to the present invention will appear more evident from the following illustrative but non-limiting description, referring to the enclosed schematic drawings, in which.

Figure 1:
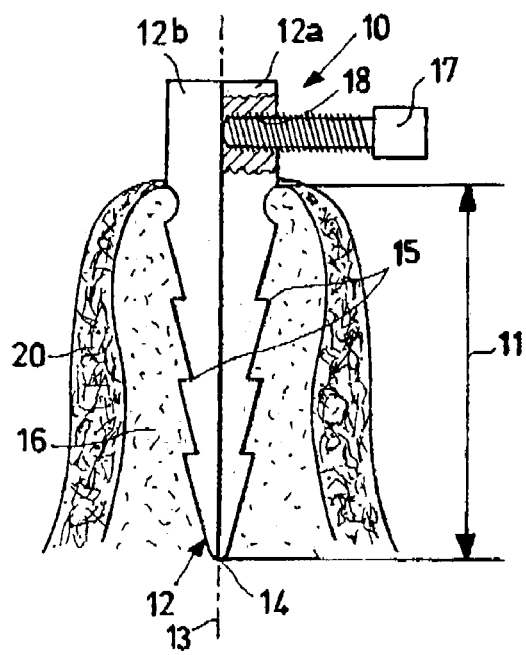
FIG. 1 is a partially sectional schematic view of a bone-dislocating device in a closed position inserted into a bone.

With reference to the figures, these illustrate a bone-dislocating device, indicated as a whole with 10, comprising a wedged body 12, subdivided into two parts 12a and 12b, specular with respect to a symmetry plane 13, substantially having a triangular section. The two parts of the wedged body 12 are, for example, joined to each other in a lower vertex 14 and have smooth facing sides and opposite knurled or stepped sides 15 which extend to a portion 11 suitable for being inserted in a bone 16. The knurled portion 15 is oriented so as to facilitate the insertion of the dislocating device 10 in the bone 16 and prevent its accidental expulsion under the pressure of the reaction forces exerted for dislocating the bone.

At an upper end, the wedged body 12 has driving elements 17, which act in a perpendicular direction to the symmetry plane 13, suitable for separating the wedged body 12, and spacing the two parts 12a and 12b.

In the embodiment illustrated in the figures, a driving screw 17 is inserted in a threaded hole 18 of a first part 12a of the wedged body and is firmly rested against a wall 19 of the opposite part 12b. In a different embodiment, not shown, the end of the screw 17 can be lodged in a housing.

The bone-dislocating device 10, object of the present invention is made of a material capable of resisting mechanical stress, for example surgical steel or a hypo-allergenic biocompatible material such as titanium.

In particular, the bone-dislocating device 10 must not cause any significant inflammatory processes in situ during the period in which it is inserted in the patient's mouth.

The bone-dislocating device 10 can be applied in both the maxillary bone and jaw bone, on the left or right side, as it has a so-called universal shape.

In order to insert the device into the bone 16, an incision is made in the paracrestal soft tissues, a gum 20, and an incision is made, with a surgical cut, in the bone tissue of a length equal to the portion of bone to be dislocated.

The dislocating device is then inserted into the bone, for example with the help of a small hammer, in a closed position, i.e. with the two parts of the wedged body 12 in contact with each other. The dislocating device is in a correction position when the portion 11, with the knurling 15, is inserted in the bone and the front end with the driving elements 17 is protruding therefrom (FIG. 1).

Figure 2:
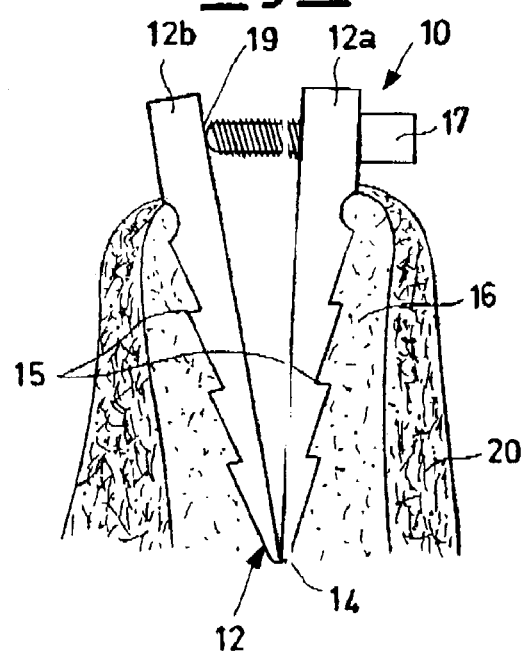
FIG. 2 is a schematic view of the device of FIG. 1 in an open activated position.
Figure 3:
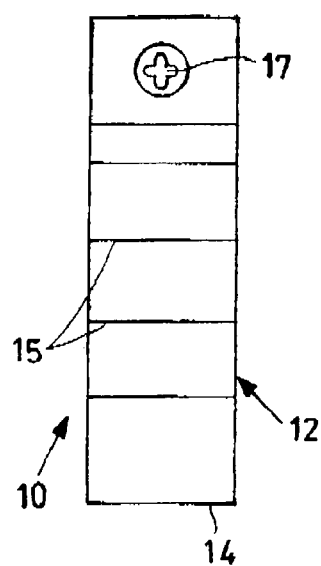
FIG. 3 is a raised side view rotated by 90° of the device of FIG. 1, removed from the bone.

The dislocation of the bone is effected by acting on the screw 17 which separates the parts 12a and 12b of the wedged body 12, forcing it against the walls of the bone 16 (FIG. 2).

The dislocation can be effected in a single session or in several successive sessions, for example after a day, at the discretion of the surgeon using one or more devices contemporaneously.

The bone-dislocating device 10 must in any case remain in the patient's mouth for a prolonged period, for example about 40 days, to allow the dislocated area and consequently bone tissue to consolidate in the desired position.

Should the device be removed immediately, a bioinert material or plant must be inserted in the same seat to act as spacer.

Finally, by acting on the activation screw 17, the device 10 is brought back to a closed position and removed from the bone.

It is then possible to proceed with the insertion of the oral osteo-integrated plant in the cavity which has formed in the bone.

The bone-dislocating device, object of the present invention, has the advantage of being only slightly invasive and causing limited traumas to the bone in which it is inserted, protecting it from degenerative phenomena, for example necrosis.

Furthermore the dislocating device can be advantageously activated progressively over a period of time at entities which can be programmed a priori by the surgeon.

The invention claimed is:

1. A bone-dislocating device (10) for insertion into a bone (16), which is a maxillary or jaw bone which is to be dislocated, said bone dislocating device comprising a wedged body (12), subdivided into two parts (12a and 12b) each of said parts having a substantially triangular section, each of said two parts (12a and 12b) of said wedged body (12) being equipped with a portion (11) to be inserted in said bone (16), each of said two parts (12a and 12b) being joined to a lower apex (14), said portion (11) being provided with a knurled section (15) for facilitating the insertion of said dislocating device (10) into said bone (16) and preventing its accidental expulsion under the pressure of the reaction forces exerted to dislocate said bone (16) said wedged body (12) being equipped with driving elements (17) located close to an upper end, said driving elements consisting of a driving screw (17) being adapted for spacing the two parts (12*a* and 12*b*) of the wedged body (12) said driving screw (17) being inserted in a threaded hole (18) of one part (12*a* or 12*b*) and with an end of said driving screw (17) firmly resting against an opposite part (12*b* or 12*a*) of said wedged body (12).

* * * * *